United States Patent
Stanlake

(10) Patent No.: US 9,823,311 B2
(45) Date of Patent: Nov. 21, 2017

(54) SYSTEM TO IDENTIFY POTENTIAL ELECTRICAL NETWORK FAULTS COMBINING VIBRATION AND POWER QUALITY ANALYSIS

(71) Applicant: SCHNEIDER ELECTRIC USA, INC., Palatine, IL (US)

(72) Inventor: Matthew Stanlake, Victoria (CA)

(73) Assignee: SCHNEIDER ELECTRIC USA, INC., Andover, MA (US)

( * ) Notice: Subject to any disclaimer, the term of this patent is extended or adjusted under 35 U.S.C. 154(b) by 176 days.

(21) Appl. No.: 14/448,131

(22) Filed: Jul. 31, 2014

(65) Prior Publication Data
US 2016/0033583 A1    Feb. 4, 2016

(51) Int. Cl.
| | |
|---|---|
| *G01R 31/40* | (2014.01) |
| *G01N 29/04* | (2006.01) |
| *G01R 31/02* | (2006.01) |
| *G08B 21/18* | (2006.01) |
| *G01R 31/34* | (2006.01) |
| *G01R 19/25* | (2006.01) |
| *G01R 31/08* | (2006.01) |

(52) U.S. Cl.
CPC ............. *G01R 31/40* (2013.01); *G01N 29/04* (2013.01); *G01R 19/2513* (2013.01); *G01R 31/021* (2013.01); *G01R 31/343* (2013.01); *G08B 21/185* (2013.01); *G01R 31/086* (2013.01); *Y04S 10/522* (2013.01)

(58) Field of Classification Search
CPC ........ G01R 31/02; G01R 31/40; G01N 29/04; G08B 21/18
See application file for complete search history.

(56) References Cited

U.S. PATENT DOCUMENTS

| | | | |
|---|---|---|---|
| 2010/0156649 A1* | 6/2010 | Deaver, Sr. ...... | G01R 19/16547 340/646 |
| 2011/0270450 A1 | 11/2011 | Gujjar et al. | |
| 2012/0046891 A1* | 2/2012 | Yaney ................. | G08B 25/06 702/62 |
| 2012/0093647 A1* | 4/2012 | Bengtson ............ | G05B 15/02 416/61 |
| 2012/0143565 A1 | 6/2012 | Graham, III et al. | |
| 2014/0025211 A1* | 1/2014 | Cheim ................ | G05B 13/02 700/286 |

OTHER PUBLICATIONS

Extended European Search Report from corresponding European Application No. 15178257.0 dated Nov. 30, 2015.

* cited by examiner

*Primary Examiner* — Jermele M Hollington
*Assistant Examiner* — Zannatul Ferdous
(74) *Attorney, Agent, or Firm* — Lando & Anastasi, LLP

(57) ABSTRACT

A system to identify potential faults in an electrical power distribution system includes a vibration monitor configured to detect a vibration event proximate a portion of the electrical power distribution system, a power quality monitor configured to detect a power quality event in a portion of the electrical power distribution system, an analysis system configured to correlate the vibration event detected by the vibration monitor with the power quality event detected by the power quality monitor, and an output configured to receive information regarding the power quality event from the analysis system and to provide the information to an operator.

20 Claims, 8 Drawing Sheets

SYSTEM TO IDENTIFY POTENTIAL ELECTRICAL NETWORK FAULTS COMBINING VIBRATION AND POWER QUALITY ANALYSIS

BACKGROUND

1. Field of Invention

Aspects and embodiments of the present disclosure are directed to systems and methods for detecting potential faults in an electrical power distribution system.

2. Discussion of Related Art

Electrical maintenance engineers are often tasked with detecting and correcting problems in electrical power distribution systems before these problems become catastrophic faults. One problem faced by electrical maintenance engineers is to locate and repair unsecure connections in an electrical power distribution system so that the unsecure connection may be repaired before it fails completely. Unsecure connections may include, for example, a loose bolt on a busbar, a poorly connected circuit breaker, a corroded electrical connection, or a connection that the vibration of associated or nearby equipment has worked loose over time.

One tool at the electrical maintenance engineer's disposal for detecting problems in electrical power distribution systems is the use of infrared cameras to analyze equipment. Infrared cameras may be utilized to detect problems such as loose connections or corrosion in an electrical connection because these problems typically increase the resistance of the electrical connection thereby increasing the temperature at the location of the problem. Using an infrared camera helps a maintenance engineer to see if there could be a problem developing in a portion of an electrical power distribution system that is not otherwise visually apparent. FIG. 1 shows an example where a loose connection is causing the top wire illustrated in the figure to heat more than the other wires. If a problem which results in localized heating is detected by inspection with an infrared camera, the electrical maintenance engineer will know where to focus efforts to correct the problem.

Manual inspection with infrared cameras, however, is not an ideal solution for detecting and correcting problems in electrical power distribution systems. Manual inspection with infrared cameras does not provide continuous monitoring to the electrical power distribution system. Operators will often perform an infrared analysis on key equipment once a year, or once every several years. Further, electrical maintenance engineers can only analyze what they can see. Switchgear cabinets often have only a small port through which electrical maintenance engineers can perform infrared inspection of systems within the cabinets. FIG. 2 illustrates an example of a switchgear cabinet including a viewing port through which an electrical maintenance engineer is performing an infrared inspection. In many instances, the majority of the connections in an electrical power distribution system are hidden from view, and unable to be inspected visually. For example, electrical connections located in sealed conduits may not be visually accessible at all. Manual inspection of an electrical power distribution system with infrared cameras is also time consuming. The electrical maintenance engineers may also be required to ensure that an electrical power distribution system under inspection is sufficiently loaded, for example, at 40% of peak load or more, to cause heat build-up in the system at locations of potential imminent faults.

Another tool electrical maintenance engineers may have at their disposal are power monitoring systems. A power monitoring system may collect power quality and energy data from monitoring devices throughout an electrical power distribution system and may allow operators to analyze potential problems, for example, power quality events, power factor, or harmonics. This data could indicate potential problems in the electrical distribution system itself or could indicate problems with either the electrical supplier (utility) or consumers of the energy. In some instances, a power monitoring system may highlight the same types of problems as infrared analysis by measuring electrical parameters of an electrical system, instead of relying on a visual inspection. Understanding how to correlate the large volume of power data a power monitoring system may collect with potential electrical faults which should be addressed can be a challenge.

Yet another tool maintenance engineers may utilize is a vibration analysis system. Vibration analysis systems, rather than being used to monitor electrical power parameters of an electrical power distribution system, may be used to monitor major assets such as large motors or key pieces of machinery. Vibration monitors in a vibration analysis system can detect imbalances in a machine or motor that could indicate potential failures in components such as bearings or brushes.

SUMMARY

In accordance with an aspect of the present disclosure, there is provided a system to identify potential faults in an electrical power distribution system. The system comprises a vibration monitor configured to detect a vibration event proximate a portion of the electrical power distribution system, a power quality monitor configured to detect a power quality event in a portion of the electrical power distribution system, an analysis system configured to correlate the vibration event detected by the vibration monitor with the power quality event detected by the power quality monitor, and an output configured to receive information regarding the power quality event from the analysis system and to provide the information to an operator.

In some embodiments, the system further comprises a vibration monitoring system configured to receive data regarding the vibration event from the vibration monitor and to timestamp the data regarding the vibration event. The system may further comprise a power quality monitoring system configured to receive data regarding the power quality event from the power quality monitor and to accurately timestamp the data regarding the power quality event. The system may further comprise a time synchronizer configured to provide time data to both the vibration monitoring system and the power quality monitoring system. The time synchronizer may be calibrated by receiving time data from a global positioning system satellite.

In some embodiments, the system further comprises a plurality of power quality monitors configured to provide an indication of a location of the power quality event. The system may further comprise an input device configured to receive an indication from an operator of a priority level of the power quality event and to transmit the indication to the analysis system. The analysis system may be configured to learn to classify a priority of a subsequent power quality event responsive to the indication from the operator. The analysis system may be configured to classify the priority of the subsequent power quality event responsive to analysis of a severity of the power quality event and a type of equipment affected by the power quality event.

In accordance with another aspect of the present disclosure, there is provided a system to identify potential faults in an electrical power distribution system. The system comprises a first input configured to receive vibration data associated with a vibration event proximate a portion of the electrical power distribution system from a vibration monitor, a second input configured to receive power quality data associated with a power quality event in a portion of the electrical power distribution system from a power quality monitor, and an output configured to display information regarding the power quality event responsive to the system establishing a correlation between the vibration event and the power quality event.

In accordance with another aspect of the present disclosure, there is provided a method for identifying potential faults in an electrical distribution system. The method comprises detecting a vibration event proximate a portion of the electrical distribution system utilizing a vibration monitor, detecting a power quality event in a portion of the electrical distribution system utilizing a power quality monitor, correlating the vibration event detected by the vibration monitor with the power quality event detected by the power quality monitor, and outputting information regarding the power quality event to an operator.

In some embodiments, the method further comprises determining a location of the vibration event by performing a triangulation analysis of data provided from multiple vibration monitors. The method may further comprise determining a location of the power quality event from power quality data provided from multiple power quality monitors. Correlating the vibration event detected by the vibration monitor with the power quality event detected by the power quality monitor may comprise adding a timestamp to vibration event data associated with the vibration event provided by the vibration monitor, adding a timestamp to power quality event data associated with the power quality event provided by the power quality monitor, and comparing the timestamp of the vibration event data to the timestamp of the power quality event data. The vibration monitor may generate the timestamp of the vibration event data responsive to receipt of time data from a time synchronizer and the power quality monitor may generate the timestamp of the power quality event data responsive to receipt of time data from the time synchronizer.

In some embodiments, the method further comprises receiving, by an analysis block, an indication from an operator of a priority level of the power quality event. The method may further comprise assigning a priority level with the power quality event based on a parameter of the power quality event, the indication from the operator, and a type of equipment affected by the power quality event. The method may further comprise assigning a priority level to a subsequent power quality event based on the priority level assigned to the power quality event. The method may further comprise determining an action to take responsive to detection of the subsequent power quality event based on the priority level assigned to the subsequent power quality event. Determining the action to take may include determining whether to communicate an indication of the subsequent power quality event to the operator.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
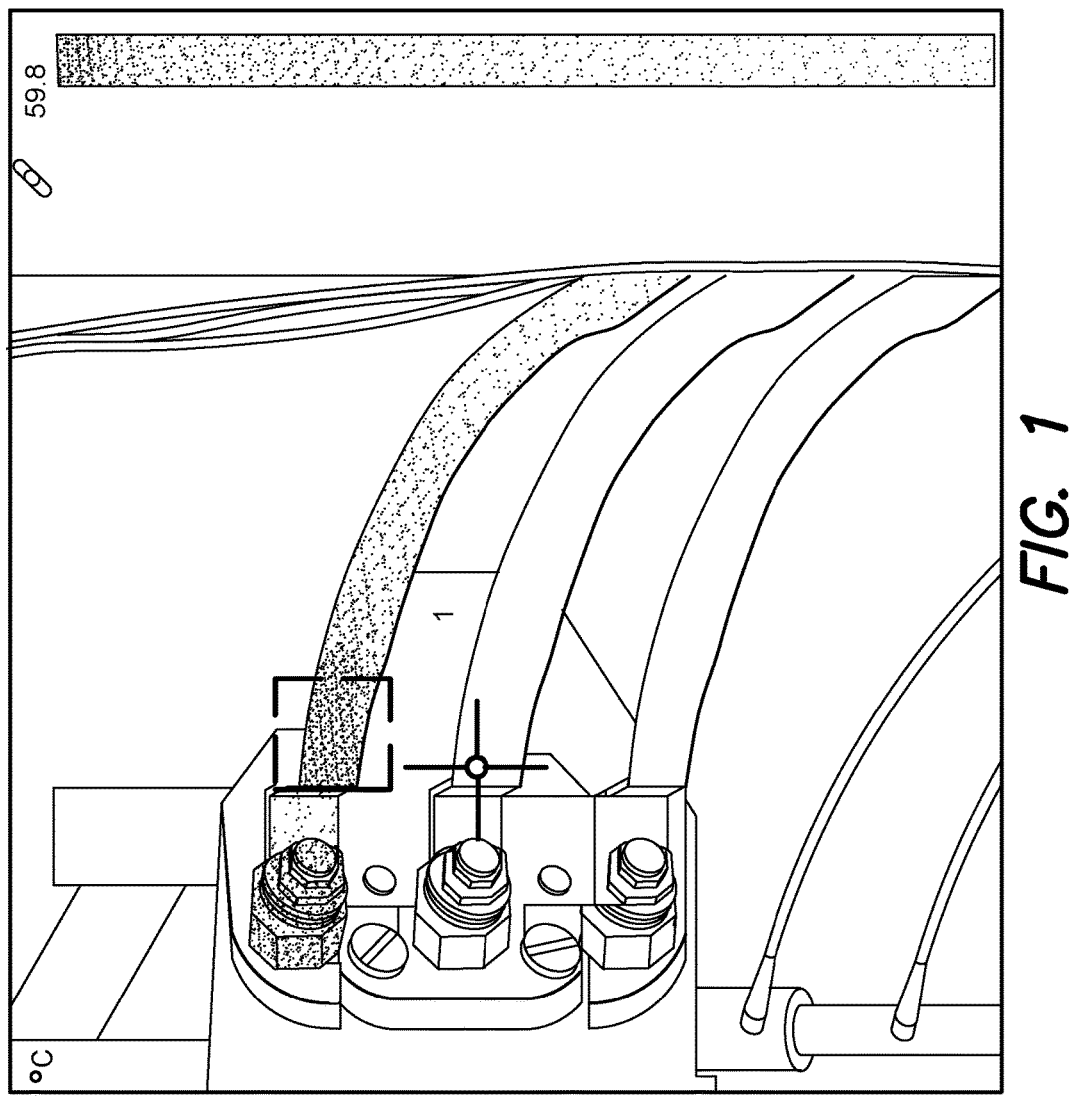
FIG. 1 is an illustration of an infrared image of a portion of an electrical power distribution system indicating a hot spot in a wire of the system.
Figure 2:
FIG. 2 is an illustration of how an electrical maintenance engineer may gather an infrared image of a portion of an electrical power distribution system in a switchbox.

This disclosure is not limited in its application to the details of construction and the arrangement of components set forth in the following description or illustrated in the drawings. The disclosed systems and methods are capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Various aspects and embodiments disclosed herein include systems and methods for continuously monitoring an electrical power distribution system for potential problems. Aspects and embodiments disclosed herein may be adapted for use to monitor electrical power distribution systems, also referred to herein as "electrical grids," "electrical networks," or simply "electrical systems," in facilities such as factories, office buildings, residential buildings, or throughout a municipality. Aspects and embodiments disclosed herein are not limited for use in any particular electrical power distribution system.

Aspects and embodiments disclosed herein give maintenance personnel a way to continuously monitor an electrical power distribution system for potential problems by correlating vibration events with subsequent or simultaneously occurring power quality events. Electrical power distribution system problems, for example, loose or corroded wiring connections can take time to develop. If a problem area of an electrical power distribution system experiences a vibration event, an associated power quality event may be exhibited for a short period of time, for example, for a fraction of a second after or concurrent with the vibration event. The vibration event might not cause a complete failure, but it might cause enough change in a parameter of power flowing through a problem area, for example, a loose or corroded electrical connection, to be detectable by a power quality (PQ) monitoring system. If a PQ event occurs shortly, for example, milliseconds after a vibration event it could indicate a potential problem, for example, a loose connection or corrosion that has not yet completely failed, but if left unaddressed could reach a catastrophic failure stage. Using the features of the PQ monitoring system an electrical maintenance engineer, operator, or other user of the system can pinpoint where the problem occurred in the electrical power distribution system and investigate that area and correct the problem prior to the occurrence of catastrophic failure. Aspects and embodiments disclosed herein may act as an early warning system, identifying and finding problems before they become catastrophic faults, for example, a complete failure of an electrical connection. Aspects and embodiments disclosed herein may also streamline the manual investigation process by pointing engineers or maintenance personnel to the exact point of concern. Aspects and embodiments disclosed herein may solve various problems with infrared analysis. For example, aspects and embodiments disclosed herein may operate continuously, allowing problems to be found at any time, not just during periodic manual visual analysis. Further, aspects and embodiments disclosed herein may detect events that occur anywhere over the entire electrical power distribution system, not just in components visible through infrared investigation windows or otherwise easily accessible.

Aspects and embodiments disclosed herein may also solve a problem observed in many power quality monitoring systems. Aspects and embodiments disclosed herein may assist operators in identifying which events or data should be followed up on and which can be safely ignored or de-prioritized. PQ monitoring systems may collect a huge amount of data. Turning that data into useful information, for example, to identify potential problems which have not yet resulted in compete failure, but which should be addressed to prevent a possible failure event from occurring can be very challenging. In some instances, major PQ events indicative of a point of failure in an electrical distribution system may be readily identified by a PQ system, however, events that may be too minor to factor into typical analysis cycles, but which may be indicative of an imminent failure, may not be identified. It is these minor events, if correlated with a vibration event, that can be prioritized higher in an electrical maintenance engineer's investigate list, allowing the electrical maintenance engineer to perform predictive maintenance rather than just preventative maintenance.

Figure 3:
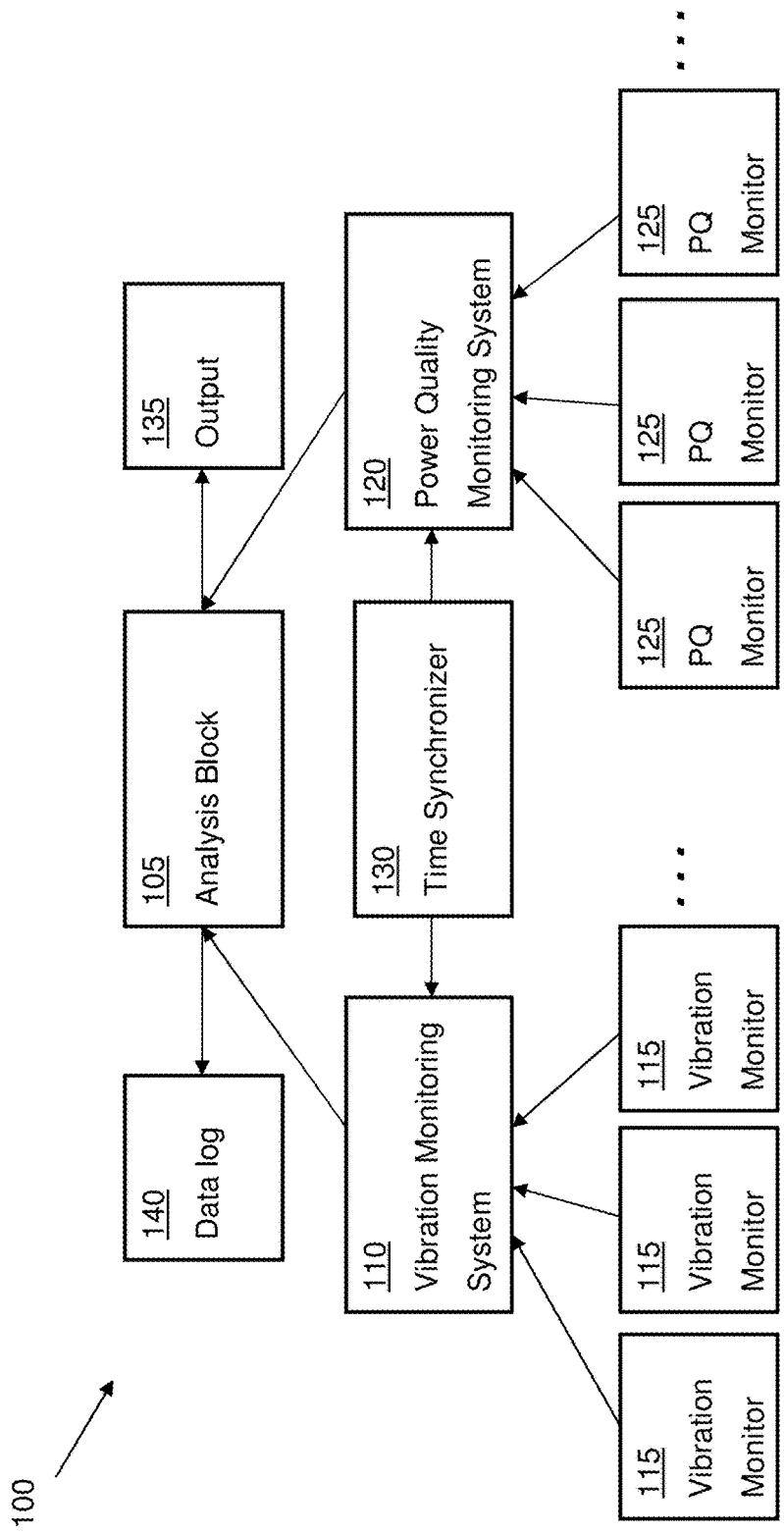
FIG. 3 is a block diagram of an embodiment of a system for detecting potential faults in an electrical power distribution system.

An embodiment of a system to identify potential electrical power distribution system faults is illustrated in a block diagram in FIG. 3, indicated generally at 100. The system 100 includes an analysis block 105, a vibration monitoring system 110 and associated vibration monitors 115, a power quality monitoring system 120 and associated PQ monitors 125, a clock or time synchronizer 130, an output system 135, and a data logging or recording system 140. The analysis block 105 queries the power quality monitoring system 120 and the vibration monitoring system 110 for event information and determines when correlations exist between events detected by the power quality monitoring system 120 and the vibration monitoring system 110. The analysis block 105 sends results of event analysis to a user through the output system 135 using, for example, e-mail, visual screens which may potentially be connected to other site management systems, or visual alerts, for example, a flashing light. The analysis block 105 is also responsible for a machine learning aspect of the system whereby feedback from operators is associated with event information to, for example, determine an appropriate priority or severity rating to assign a particular detected event. For example, as is explained in greater detail below, if an operator provides feedback on false-positive events, the system can factor this information into future recommendations and learn for which events to alert operators, which events to add to a low-priority maintenance log, and which events can be safely ignored.

The vibration monitoring system 110 collects continuous data feeds from the vibration monitors 115 throughout a location in which an electrical power distribution system being monitored is present. The vibration monitors 115 may include accelerometers, for example, micro-electrical mechanical system (MEMS) accelerometers or other forms of vibration monitors known in the art. Suitable vibration monitors are available from companies including Bentley Nevada, Data Physics Corporation, SKF, and Emerson. The vibration monitors 115 and vibration monitoring system 110 may communicate via a wired or a wireless connection. The vibration monitoring system 110 constantly monitors the vibrations in the system and will capture a vibration event when a vibration detected at a vibration monitor 115 exhibits a statistically significant deviation from the normal vibration at that location. This use of deviation analysis helps to filter out spurious events that might occur in industrial settings where a certain amount of vibrations are always occurring due to the machinery being operated and the process being performed.

A vibration event may be caused by any of numerous occurrences. Some vibration events may be caused by natural occurrences, for example, a seismic event or by wind from a storm causing vibration in a facility in which an electrical power distribution system being monitored is present. Other vibration events may be manmade, for example, by low flying aircraft, by road vehicles passing the facility in which the electrical power distribution system being monitored is present, by operators of the facility passing by a vibration monitor, or by vibrations generated by other equipment within the facility.

Each vibration event that is detected by the system 100 is time stamped with the event time, in some embodiments to millisecond accuracy. The event time may be determined by a clock internal to the vibration monitoring system 110 or by an external clock or time synchronizer 130 which is shared between the vibration monitoring system 110 and the PQ monitoring system 120. In some embodiments, the time synchronizer 130 may include a global positioning system (GPS) time synchronization component. The time synchronizer 130 ensures that the timestamps of vibration events and power quality events can be compared accurately. In some embodiments, a vibration monitor 115 may be directly connected to the time synchronizer 130 to eliminate any lag that may occur between the vibration monitoring system 110 and the vibration monitor 115 itself. In some embodiments, a PQ monitor 125 may be directly connected to the time synchronizer 130 to eliminate any lag that may occur between the PQ monitoring system 110 and the PQ monitor 125 itself.

The PQ monitoring system 120 connects to the PQ monitors 125 throughout the location in which the electrical power distribution system being monitored is present. The connection between the PQ monitoring system 120 and the PQ monitors 125 may be a wired or a wireless connection. The PQ monitors 125 continually monitor and, in some embodiments, analyze the power characteristics of the electrical power distribution system at the point where they are installed. Examples of suitable PQ monitors include PowerLogic® ION 7650, PowerLogic® CM 4000, and PowerLogic® PM 850 PQ monitors available from Schneider Electric. The PQ monitors 125, directly, and/or through the PQ monitoring system 120 are connected to the time synchronizer 130 to ensure that any observed PQ events can be accurately correlated to vibration events detected by the vibration monitoring system 110.

A PQ event may include a change, transient or permanent, in one or more parameters of power passing through a portion of an electrical power distribution system being monitored. PQ events may include, for example, sags or interruptions in power, voltage, or current through a portion of the electrical power distribution system, electrical interference causing electrical noise in a portion of the electrical power distribution system, or electrical noise caused by a loose or corroded electrical connection. PQ events may include, for example, changes to a frequency and/or phase of alternating current power through a portion of the electrical power distribution system, or changes in an amount of reflected or absorbed power from a piece of equipment connected to the electrical power distribution system. PQ events may be caused by equipment or events internal to or proximate a facility in which an electrical power distribution system being monitored is present. For example, a PQ event may be caused by a large current draw from a piece of equipment starting up or by electromagnetic interference from a piece of equipment in the facility. PQ events may also or alternatively be caused by events external to the facility, for example, due to problems at a power supply utility, problems with a power transmission line to the facility, or by an event such as a lightning strike.

FIG. 3 illustrates three vibration monitors 115 and three PQ monitors 125. It should be understood, however, that in different embodiments, different numbers of vibration monitors 115 and/or PQ monitors 125 may be utilized. Further, although illustrated as discreet elements, in different embodiments, any one or more of the elements of the illustrated system 100 may be combined. For example, in some embodiments, the PQ monitoring system 120 and vibration monitoring system 110 may be combined into one computer system, the vibration monitors 115 and PQ monitors 125 may be combined into composite vibration/power quality monitors, or the time synchronizer 130 may be included in the same computer system as the analysis block 105.

Figure 4:
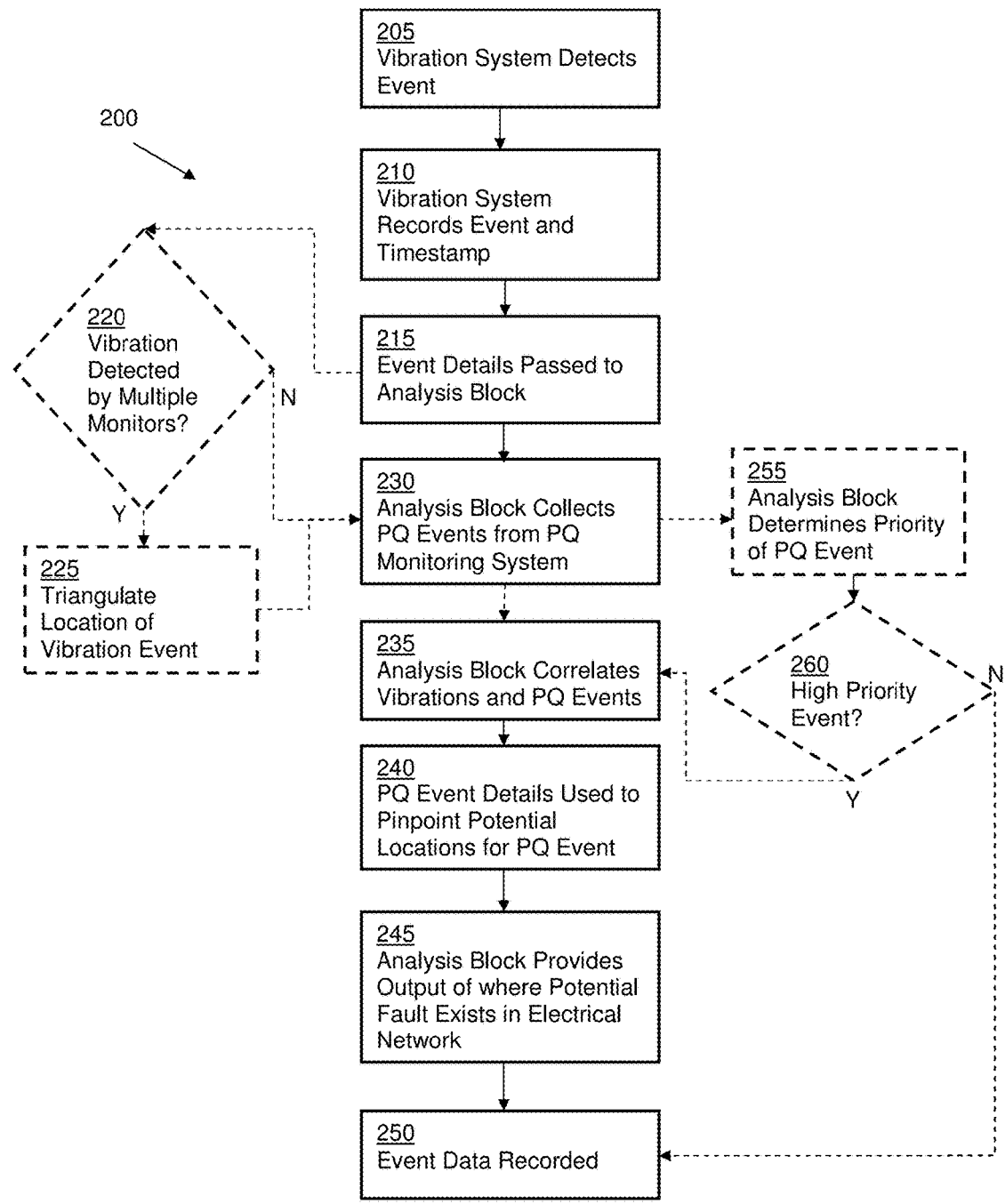
FIG. 4 is a flow chart of an embodiment of a method for detecting potential faults in an electrical power distribution system.

An embodiment of a method of operating the system 100 of FIG. 3 is illustrated in FIG. 4, generally at 200. The method 200 includes detecting vibration events and correlating the vibration events with PQ events. In act 205, a vibration monitor 115 in the system 100 detects a vibration event. As discussed previously, a vibration event is an occurrence of vibration that deviates in intensity and/or frequency from the statistically expected range of values for that monitor. A trigger point for a parameter of vibration, for example, frequency or intensity, which should cause a detected vibration to be flagged as a vibration event may be adjusted, for example, based on the tolerance for vibration of a particular facility or electrical power distribution system.

One of ordinary skill in the art of process control would be able to set control limits (for example, statistical process control limits) around parameters of a baseline set of vibration readings which when violated, would be an indication of a statistically significant vibration event having occurred. In some embodiments, control charts for vibration readings from a vibration monitor 115 may be established and data points for vibration intensity and/or frequency readings plotted on these control charts. For example, readings from a vibration monitor 115 under normal operating conditions could be monitored and from the vibration data obtained, means and standard deviations for vibration measurement parameters from the vibration monitor 115 could be calculated and utilized to construct a control chart for the vibration data for the vibration monitor 115. In some embodiments, a different control chart may be created for each individual vibration monitor 115. The control charts may include virtual control charts within a vibration monitor 115, vibration monitoring system 110, and/or analysis block 105. If the plotted data points violated one or more statistical process control (SPC) rules, this would be indicative of a vibration event having occurred.

In some embodiments, control charts could be established and plotted data points monitored for violations of one or more of the Western Electric SPC rules. These rules are as follows:

1) One Point Outside Upper or Lower Control Limits

The Upper and Lower Control Limits are set at three standard deviations from the mean. If a point lies outside either of these limits, there is only a 0.3% chance that this was caused by the normal process.

2) Eight Points on the Same Side of the Mean

There is an equal chance that any given point will fall above or below the mean. The chance that a point falls on the same side of the mean as the one before it is one in two. The odds that the next point will also fall on the same side of the mean is one in four. The probability of getting eight points on the same side of the mean is only around 1%.

3) Eight Points Increasing or Decreasing

The same logic is used here as for "Eight Points on the Same Side of the Mean." Sometimes this rule is changed to seven points rising or falling.

4) Two of Three Points outside Warning Limits

The Warning Limits are usually set at two standard deviations (i.e. two sigma) from the mean. The probability that any point will fall outside the warning limit is only 5%. The chances that two out of three points in a row fall outside the warning limit is only about 1%.

5) Four of Five Points Falling Outside One Sigma

In normal processing, 68% of points fall within one sigma of the mean, and 32% fall outside it. The probability that 4 of 5 points fall outside of one sigma is only about 3%.

6) Fourteen Points Alternating Direction

This rule treats each pair of adjacent points as one unit. The chances that the second point is always higher than (or always lower than) the preceding point, for all seven pairs, is only about 1%.

7) Fifteen Points in a Row within One Sigma

In normal operation, 68% of points will fall within one sigma of the mean. The probability that 15 points in a row will do so is less than 1%.

8) Eight Points in a Row Outside One Sigma

Since 68% of points lie within one sigma of the mean, the probability that eight points in a row fall outside of the one-sigma line is less than 1%.

In other embodiments, control charts could be utilized in which violations of one or more of the Wheeler or Nelson SPC rules (which are well known to those familiar with statistical process control) could be used as an indicator of a vibration event having occurred.

When the vibration monitor 115 detects a vibration event, information about the location and metadata about the vibration event, for example, magnitude, frequency, and/or duration, is passed to the vibration monitoring system 110. The vibration monitoring system 110 timestamps the vibration event using a timestamp acquired from the time synchronizer 130 (act 210). The vibration event data is then passed to the analysis block 105 for further analysis (act 215).

In some embodiments, once the analysis block 105 has the vibration event information, it first performs a meta-analysis to determine if multiple vibration monitors 115 recorded a vibration event at the same time or at times sufficiently close to one another (for example, a time defined by the distance between the multiple vibration monitors 115 and the speed of sound) that it is likely that the same vibration event was sensed by each of the multiple vibration monitors 115 (act 220). In some embodiments, a location of the vibration event could be triangulated from vibration data from the multiple vibration monitors 115. While not completely necessary for finding potential connection issues in the electrical power distribution system, being able to triangulate the source of the vibration event (act 225) from the vibration event data from the multiple vibration monitors 115 could be useful for maintenance personnel to detect the source or recurring cause of anomalous vibrations. Upon detecting the source or recurring cause of anomalous vibrations, maintenance personnel may take actions to repair faulty equipment which may be causing the anomalous vibrations or take actions to otherwise remediate or eliminate the anomalous vibrations.

Once the vibration event information has been received by the analysis block 105 and/or after performance of the meta-analysis and triangulation of the vibration event data, the PQ monitoring system 120 is queried for PQ events that occurred during or shortly after the vibration event (act 230). If the PQ monitoring system 120 reports one or more PQ events that occurred during or shortly after the vibration event, the analysis block 105 then correlates these PQ event(s) with the vibration events to find if they occurred at or near the same time (act 235). If a correlation in time exists between the vibration event and PQ event(s), the analysis block determines the location of the PQ event(s) using information included in the PQ event metadata provided from the PQ monitor(s) 125 (act 240). The location of the PQ event(s) may be determined using directional sensing capabilities of the PQ monitors 125. In some embodiments, the PQ monitors 125 are able to determine if a PQ event occurred electrically upstream or downstream of the PQ monitors 125. This information is provided to the analysis block 105 as part of the PQ event metadata. As used herein, the terms "upstream" and "downstream" denote opposite sides of a PQ monitor 125 in an electrical power distribution system.

Figure 6:
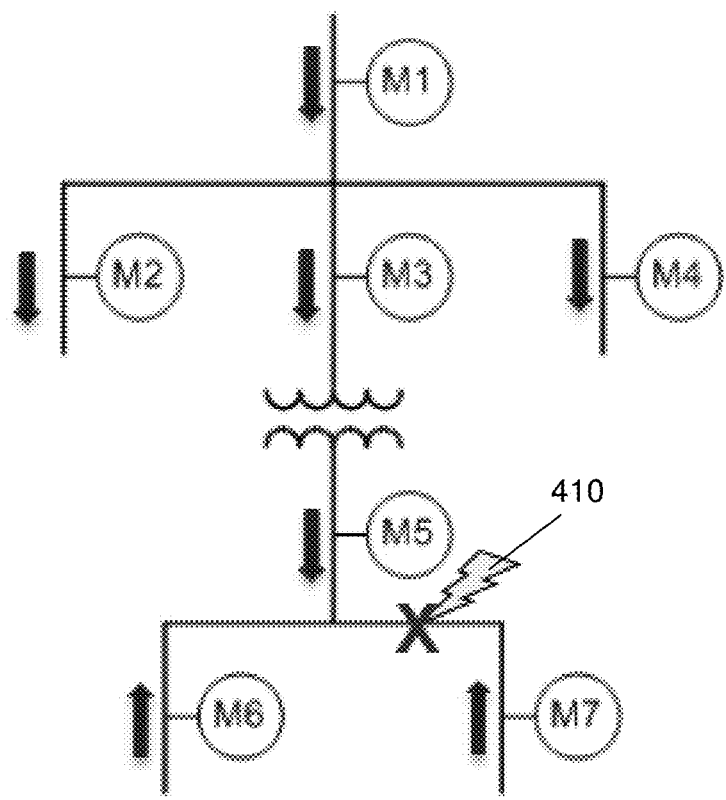
FIG. 6 is a schematic diagram of a portion of an electrical power distribution system.

FIG. 6 shows how the analysis block 105, knowing the hierarchy and relationship between the PQ monitors 125, can rapidly determine where in the electrical power distribution system a PQ event occurred. As illustrated in FIG. 6, a PQ event 410 is detected electrically downstream of PQ monitors M1, M2, M3, M4, and M5 and electrically upstream of PQ monitors M6 and M7. The analysis block 105 thus may determine that the PQ event 410 occurred somewhere between PQ monitors M6 or M7 and PQ monitor M5. The analysis block 105 may access location information for each of the PQ monitors M5, M6, and M7 and provide an indication to an operator of a likely location of the PQ event (act 245 of FIG. 4). As discussed above, this indication may be through text messages, e-mail, visual alerts, or updates to screens within an existing management system.

Alternatively, the analysis block 105 may provide an operator an indication of which PQ monitors 125 the PQ event 405 likely occurred between and the operator could determine the location of the relevant PQ monitors 125. The location information for the PQ monitors between which the PQ event likely occurred could be combined with triangulation data regarding the vibration event from the vibration monitors 115 to further narrow a range of locations for the PQ event 410 and/or vibration event.

Figure 5:
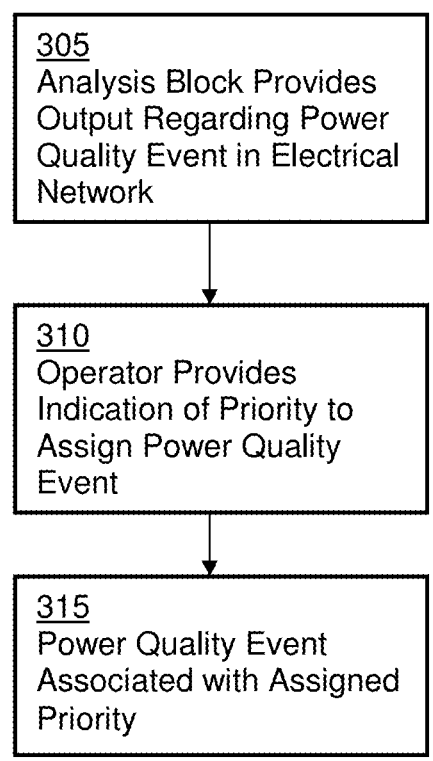
FIG. 5 is a flow chart of an embodiment of a method for detecting potential faults in an electrical power distribution system.

In some embodiments, the analysis block 105 has the ability to learn from previous events that occur within the system. An embodiment of a method by which the analysis block 105 may learn from previous events that occur within the system is illustrated generally at 300 in FIG. 5. In act 305 the analysis block 105 provides an operator with an indication of a PQ event and/or associated vibration event having occurred. After being notified of a PQ event, an operator can tag the event (act 310) with an indication of the severity and/or priority level to assign the event. Tags may include, for example, "non-issue," "low priority issue," and "high-priority issue." An operator may select a tag for an event based upon the severity of the PQ event and, in some embodiments, in consideration of the severity of the PQ event and the type of electrical system(s) affected by a PQ event detected at a particular location in the electrical distribution system.

Some electrical systems, for example, lighting or heating systems may be more tolerant to various characteristics of PQ events than more sensitive systems, for example, network data processing systems. A less sensitive system, for example, a lighting or heating system might be able to tolerate, without damage or significant disruption of operations, a voltage surge above a certain level or a power sag or interruption of a greater duration than a more highly sensitive system could. Thus, an operator may assign a lower severity or priority to a PQ event which affects a certain type or class of system on the electrical distribution system, where the operator would assign a higher severity or priority to the same PQ event if it occurred on a portion of the electrical distribution system affecting a more sensitive type or class of equipment.

In act 315, the analysis block 105 may assign the severity or priority tag selected by the operator to the PQ event indicated to the operator in act 305. The analysis block 105 may associate one or more measures of severity, for example, amount of power surge or sag and/or event duration, as well as a type of electrical system associated with a PQ monitor 125 which detected the PQ event with the PQ event. By taking this feedback into account in subsequent iterations, the analysis block 105 can adjust its communications with the user. For example, returning to FIG. 4, in some embodiments, after the analysis block 105 collects the PQ event information from the PQ event monitoring system in act 230, the analysis block 105 compares parameters of the PQ event against previous PQ events reported to an operator. The analysis block 105 determines, taking into an account a type or class of electrical system likely to be affected by the portion of the electrical distribution system including the PQ monitor(s) 125 which provided the indication of the PQ event in act 230 and the severity of the PQ event (for example, amount of power sag or duration of the event), a likely priority an operator would assign to the event (act 255). If the analysis block 105 determines that the PQ event should be assigned a low priority, or in some embodiments either a low or a medium priority, the event may simply be recorded in a PQ event log (act 250). If the analysis block determines that the PQ event should be assigned a high priority, or in some embodiments, either a high or a medium priority, the analysis block may cause the remaining acts 235, 240, 245 of the method 200 to be performed.

In some embodiments, a PQ monitor 125 may be associated with a mains electrical utility line of a facility. Utilizing the PQ monitor 125 associated with the mains electrical utility line of a facility, it would be possible to differentiate PQ events that occur outside the bounds of the facility from those that occur within the facility, making it much simpler to identify potential electrical distribution problems within the facility which are exacerbated by vibration events. Further, the analysis block 105 may be configured to analyze parameters of a PQ event to determine if the PQ event was likely caused by an electrical utility fault or by a fault internal to the electrical power distribution system of the facility. Oftentimes utility-side power sags have a simple magnitude change for the duration of the sag, while vibration-driven events have additional high-frequency components caused by the vibration. When the analysis block 105 receives a PQ signature it can compare it to known signatures to determine if the likely cause of the event was a vibration or a utility-side power sag. The analysis block 105 may provide its determination of the source of the PQ event to an operator, who may indicate to the analysis block if the determination was correct or not. Over time as PQ events are classified and stored in a database, the analysis block 105 may learn to rapidly identify potential loose connections or other electrical connection problems within the facility using just the PQ monitoring system 120.

In some embodiments, PQ event signatures may be sent to a cloud-hosted site where other subscribing customers can access them to compare their events with events in library to see if they may be caused by vibrations or loose connections at their site.

In some embodiments of a PQ event and vibration event monitoring system 100, when an event occurs, the system 100 captures and correlates both vibration and PQ event data in a moving window. This allows the vibration and PQ data just prior to a PQ event to be captured along with the vibration and PQ data after the PQ event. Operators are able to configure the system to capture vibration data whenever a particular PQ attribute changed or hit a predetermined value, allowing operators to see if minor vibrations (for example, vibrations of a certain frequency) were related to the PQ event, even if the vibration was not sufficient to trigger an indication of a vibration event by a vibration monitor 115. Such a system reduces the amount of data operators need to analyze by only capturing data on exception rather than continuously.

In some embodiments, the disclosed system 100 may scale for use by a utility on a grid level. Instead of using vibration sensors, the grid operator may correlate seismic events (earthquakes) with PQ events. The PQ monitors would be spread around the grid, each connected to a synchronized time clock, for example, a GPS timesync and report back to a central power quality monitoring system. Government agencies already provide millisecond accurate timestamps of earthquake occurrences and locations. Instead of collecting vibration event data as in acts 205, 210, and 215 of method 200, the earthquake data would be recorded by a government agency. The analysis block 105 may query this earthquake data and determine if the earthquake met a sufficient level to continue the process, for example, if the earthquake had a magnitude above three on the Richter scale and occurred within 1,000 km of the grid in question. If it did, the electrical utility would perform acts similar to acts 230-260 of method 200 to determine where a potential fault existed in the grid so that repair personnel could be dispatched to repair the potential fault prior to catastrophic failure occurring.

In some embodiments, any one or more of the analysis block 105, vibration monitoring system 110, and/or power quality monitoring system 120 of the system 100 may include a computerized control system. Various aspects may be implemented as specialized software executing in a general-purpose or specialized computer system 600 such as that shown in FIG. 7. The computer system 600 may include a processor 602 connected to one or more memory devices 604, such as a disk drive, solid state memory, or other device for storing data. Memory 604 is typically used for storing programs and data during operation of the computer system 600.

Components of computer system 600 may be coupled by an interconnection mechanism 606, which may include one or more busses (e.g., between components that are integrated within a same machine) and/or a network (e.g., between components that reside on separate discrete machines). The interconnection mechanism 606 enables communications (e.g., data, instructions) to be exchanged between system components of system 600. Computer system 600 includes one or more input devices 608, for example, a keyboard, mouse, trackball, microphone, or touch screen through which an operator may issue commands or programming to the system 600, for example to provide feedback regarding the severity or priority to assign various PQ events, as described above. Computer system 600 includes one or more output devices 610, for example, a printing device, display screen, and/or speaker. The one or more output devices 610 may include the output 135 of FIG. 3. The output devices 610 may also switches which may be utilized to control the flow of power through an electrical distribution system. One or more sensors 614 may also provide input to the computer system 200. These sensors may include, for example, the vibration monitors 115 and/or the PQ monitors 125. In addition, computer system 600 may contain one or more interfaces (not shown) that connect computer system 600 to a communication network in addition or as an alternative to the interconnection mechanism 606.

Figure 8:
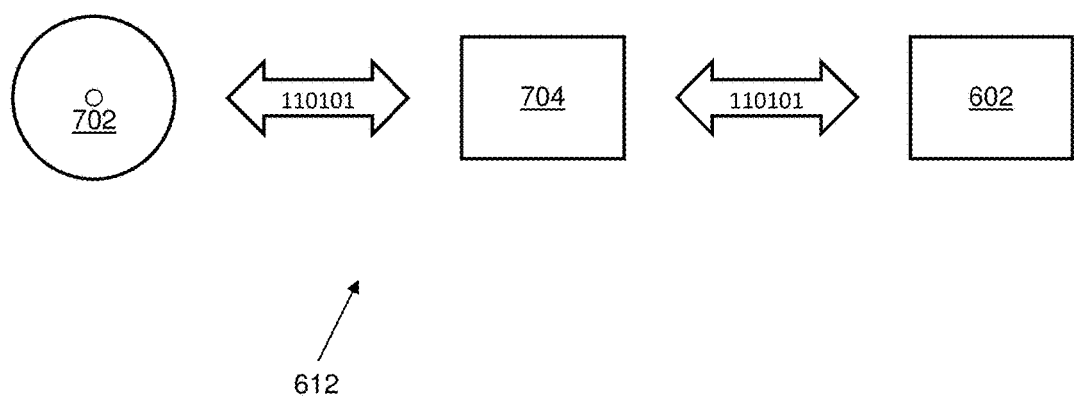
FIG. 8 is a block diagram of a memory system of the computer system of FIG. 7.

The storage system 612, shown in greater detail in FIG. 8, typically includes a computer readable and writeable nonvolatile recording medium 702 in which signals are stored that define a program to be executed by the processor or information to be processed by the program. The medium may include, for example, a disk or flash memory. Typically, in operation, the processor causes data to be read from the nonvolatile recording medium 702 into another memory 704 that allows for faster access to the information by the processor than does the medium 702. This memory 704 is typically a volatile, random access memory such as a dynamic random access memory (DRAM) or static memory (SRAM). It may be located in storage system 612, as shown, or in memory system 604. The data log 140 of FIG. 3 may be included in the nonvolatile recording medium 702 or in other portions of the memory system 604 or storage system 612. The processor 602 generally manipulates the data within the integrated circuit memory 604, 704 and then copies the data to the medium 702 after processing is completed. A variety of mechanisms are known for managing data movement between the medium 702 and the integrated circuit memory element 604, 704, and embodiments disclosed herein are not limited to any particular data movement mechanism. Embodiments disclosed herein are not limited to a particular memory system 604 or storage system 612.

The computer system may include specially-programmed, special-purpose hardware, for example, an application-specific integrated circuit (ASIC). Embodiments disclosed herein may be implemented in software, hardware or firmware, or any combination thereof. Further, such methods, acts, systems, system elements and components thereof may be implemented as part of the computer system described above or as an independent component.

Figure 7:
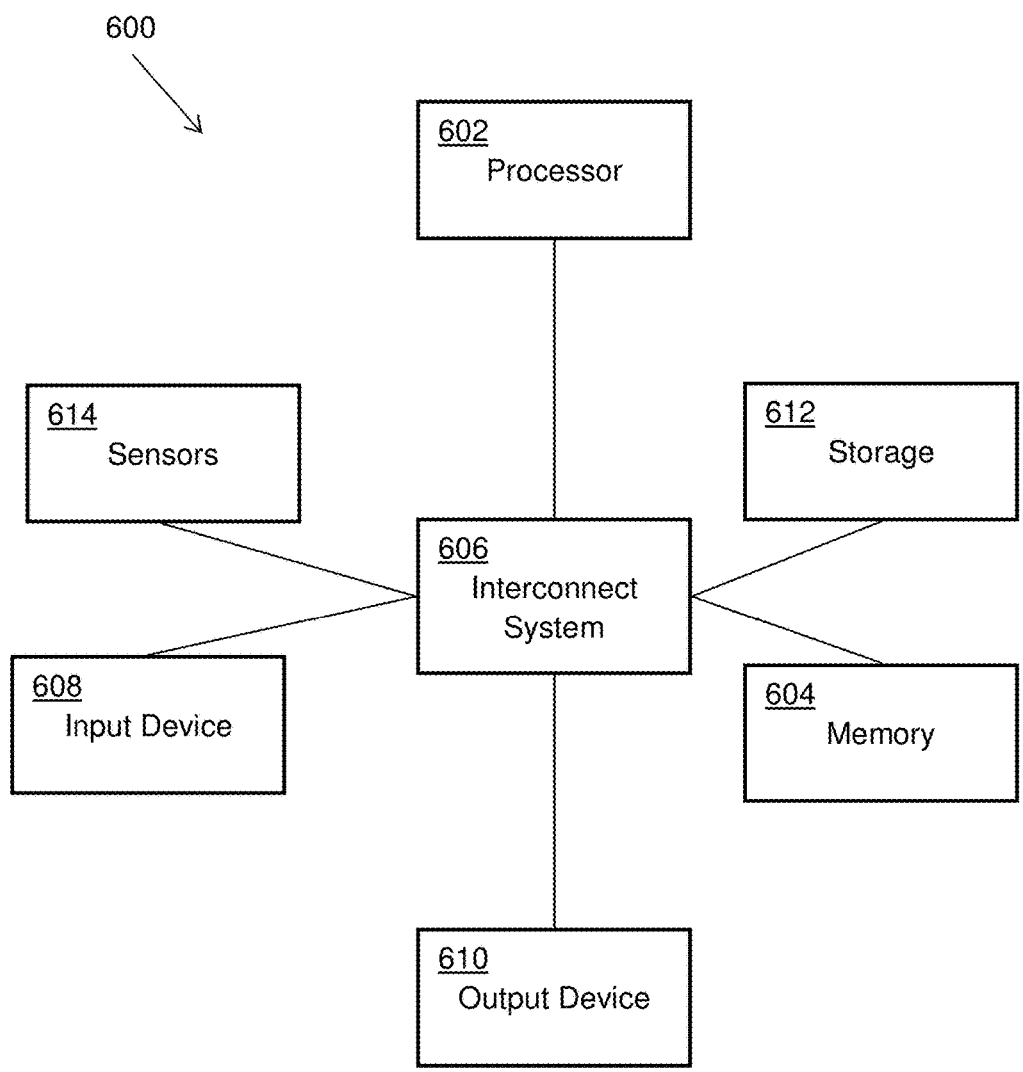
FIG. 7 is a block diagram of a computer system upon which embodiments of a method for detecting potential faults in an electrical power distribution system may be performed.

Although computer system 600 is shown by way of example as one type of computer system upon which various embodiments disclosed herein may be practiced, it should be appreciated that the embodiments disclosed herein are not limited to being implemented on the computer system as shown in FIG. 7. Various embodiments disclosed herein may be practiced on one or more computers having a different architecture or components that that shown in FIG. 7.

Computer system 600 may be a general-purpose computer system that is programmable using a high-level computer programming language. Computer system 600 may be also implemented using specially programmed, special purpose hardware. In computer system 600, processor 602 is typically a commercially available processor such as the well-known Pentium™ or Core™ class processors available from the Intel Corporation. Many other processors are available. Such a processor usually executes an operating system which may be, for example, the Windows 7 or Windows 8 operating system available from the Microsoft Corporation, the MAC OS System X available from Apple Computer, the Solaris Operating System available from Sun Microsystems, or UNIX available from various sources. Many other operating systems may be used.

The processor and operating system together define a computer platform for which application programs in high-level programming languages are written. It should be understood that embodiments disclosed herein are not limited to a particular computer system platform, processor, operating system, or network. Also, it should be apparent to those skilled in the art that the embodiments disclosed herein are not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various embodiments disclosed herein may be distributed among one or more computer systems configured to provide a service (e.g., servers) to one or more client computers, or to perform an overall task as part of a distributed system. For example, various embodiments disclosed herein may be performed on a client-server system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). In some embodiments one or more components of the computer system 600 may communicate with one or more other components over a wireless network, including, for example, a cellular telephone network.

It should be appreciated that embodiments disclosed herein are not limited to executing on any particular system or group of systems. Also, it should be appreciated that embodiments disclosed herein are not limited to any particular distributed architecture, network, or communication protocol. Various embodiments may be programmed using an object-oriented programming language, such as Small-Talk, Java, C++, Ada, or C# (C-Sharp). Other object-oriented programming languages may also be used. Alternatively, functional, scripting, and/or logical programming languages may be used. Various embodiments disclosed herein may be implemented in a non-programmed environment (e.g., documents created in HTML, XML or other format that, when viewed in a window of a browser program, render aspects of a graphical-user interface (GUI) or perform other functions). Various embodiments disclosed herein may be implemented as programmed or non-programmed elements, or any combination thereof.

Having thus described several aspects of at least one embodiment of this invention, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure, and are intended to be within the scope of the invention. Accordingly, the foregoing description and drawings are by way of example only.

What is claimed is:

1. A system to identify potential faults in an electrical power distribution system, the system comprising:
    a vibration monitor configured to detect a vibration event proximate a portion of the electrical power distribution system;
    a plurality of power quality monitors configured to detect a power quality event in a portion of the electrical power distribution system;
    an analysis system configured to correlate the vibration event detected by the vibration monitor with the power quality event detected by the plurality of power quality monitors and to determine a location of the power quality event by determining power quality monitors that the power quality event occurred between; and
    an output configured to receive information regarding the power quality event from the analysis system and to provide the information to an operator.

2. The system of claim 1, further comprising a vibration monitoring system configured to receive data regarding the vibration event from the vibration monitor and to timestamp the data regarding the vibration event.

3. The system of claim 2, further comprising a power quality monitoring system configured to receive data regarding the power quality event from the plurality of power quality monitors and to accurately timestamp the data regarding the power quality event.

4. The system of claim 3, further comprising a time synchronizer configured to provide time data to both the vibration monitoring system and the power quality monitoring system.

5. The system of claim 4, wherein the time synchronizer is calibrated by receiving time data from a global positioning system satellite.

6. The system of claim 1, further comprising an input device configured to receive an indication from an operator of a priority level of the power quality event and to transmit the indication to the analysis system.

7. The system of claim 6, wherein the analysis system is configured to learn to classify a priority of a subsequent power quality event responsive to the indication from the operator.

8. The system of claim 7, wherein the analysis system is configured to classify the priority of the subsequent power quality event responsive to analysis of a severity of the power quality event and a type of equipment affected by the power quality event.

9. A system to identify potential faults in an electrical power distribution system, the system comprising:

a first input configured to receive vibration data associated with a vibration event proximate a portion of the electrical power distribution system from a vibration monitor;

a second input configured to receive power quality data associated with a power quality event in a portion of the electrical power distribution system from a plurality of power quality monitors;

an analysis block configured to determine a location of the power quality event by determining power quality monitors that the power quality event occurred between; and an output configured to display information regarding the power quality event responsive to the system establishing a correlation between the vibration event and the power quality event.

10. A method for identifying potential faults in an electrical distribution system, the method comprising:

detecting a vibration event proximate a portion of the electrical distribution system utilizing a vibration monitor;

detecting a power quality event in a portion of the electrical distribution system utilizing a plurality of power quality monitors;

determining a location of the power quality event by determining power quality monitors that the power quality event occurred between;

correlating the vibration event detected by the vibration monitor with the power quality event detected by the plurality of power quality monitors; and outputting information regarding the power quality event to an operator.

11. The method of claim 10, further comprising determining a location of the vibration event by performing a triangulation analysis of data provided from multiple vibration monitors.

12. The method of claim 10, wherein correlating the vibration event detected by the vibration monitor with the power quality event detected by the power quality monitor comprises:

adding a timestamp to vibration event data associated with the vibration event provided by the vibration monitor;

adding a timestamp to power quality event data associated with the power quality event provided by the plurality of power quality monitors; and comparing the timestamp of the vibration event data to the timestamp of the power quality event data.

13. The method of claim 12, wherein the vibration monitor generates the timestamp of the vibration event data responsive to receipt of time data from a time synchronizer and the plurality of power quality monitors generate the timestamp of the power quality event data responsive to receipt of time data from the time synchronizer.

14. The method of claim 10, further comprising receiving, by an analysis block, an indication from an operator of a priority level of the power quality event.

15. The method of claim 14, further comprising assigning a priority level with the power quality event based on a parameter of the power quality event, the indication from the operator, and a type of equipment affected by the power quality event.

16. The method of claim 15, further comprising assigning a priority level to a subsequent power quality event based on the priority level assigned to the power quality event.

17. The method of claim 16, further comprising determining an action to take responsive to detection of the subsequent power quality event based on the priority level assigned to the subsequent power quality event.

18. The method of claim 17, wherein determining the action to take includes determining whether to communicate an indication of the subsequent power quality event to the operator.

19. The system of claim 1, configured to determine a location of the vibration event by performing a triangulation analysis of data provided from multiple vibration monitors.

20. The system of claim 9, configured to determine a location of the vibration event by performing a triangulation analysis of data provided from multiple vibration monitors.

* * * * *